United States Patent [19]

Wallace

[11] Patent Number: 4,847,243

[45] Date of Patent: Jul. 11, 1989

[54] TREATMENT FOR FESCUE TOXICOSIS IN GRAZING ANIMALS

[75] Inventor: Dennis H. Wallace, Columbia, Mo.

[73] Assignee: Merck & Co., Inc., Rahway, N.J.

[21] Appl. No.: 105,837

[22] Filed: Oct. 8, 1987

[51] Int. Cl.⁴ .................... A61K 31/70; A61K 31/335
[52] U.S. Cl. ....................................... 514/30; 514/450
[58] Field of Search ............................ 514/450, 27, 30

[56] References Cited

U.S. PATENT DOCUMENTS

| | | | |
|---|---|---|---|
| Re. 32,006 | 10/1985 | Chabala et al. | 549/264 |
| Re. 32,034 | 11/1985 | Chabala et al. | 549/264 |
| 3,950,360 | 4/1976 | Aoki et al. | 424/279 |
| 4,199,569 | 4/1980 | Chabala et al. | 424/180 |
| 4,201,861 | 5/1980 | Mrozik et al. | 536/17 A |
| 4,206,205 | 6/1980 | Mrozik et al. | 424/180 |
| 4,310,519 | 1/1982 | Albers et al. | 424/181 |
| 4,427,663 | 1/1984 | Mrozik et al. | 536/7.1 |
| 4,547,520 | 10/1985 | Ide et al. | 514/450 |

OTHER PUBLICATIONS

Schmidt et al., *Journal of Animal Science*, 55 1260–1263 (1982).
Hoveland et al., (I), *Agronomy Journal*, 22 375–377 (1980).
Hoveland et al., (II), Circular 270 from Alabama Agricultural Experimental Station, Auburn University, Alabama (1984).
Hoveland et al., (III), *Agronomy Journal*, 25 821–824 (1983).
Pederson et al., *New Zealand Journal of Experimental Agricultural*, 14 307–312 (1986).

*Primary Examiner*—Amelia Burgess Yarbrough
*Attorney, Agent, or Firm*—David L. Rose; Michael C. Sudol

[57] ABSTRACT

There is disclosed a method for the prevention of fescue toxicosis in grazing animals. Fescue toxicosis results from a grazing animal ingesting certain toxins present in or on the grass which can impair growth, reproductive performance, and is sometimes fatal. It has been discovered that the administration of ivermectin or related avermectin compounds is effective in reducing or eliminating the toxic effects of fescue endophyte ingestion.

11 Claims, No Drawings

TREATMENT FOR FESCUE TOXICOSIS IN GRAZING ANIMALS

BACKGROUND OF THE INVENTION

Tall fescue has good forage quality for grazing animals in that it has adequate crude protein and satisfactory digestabilty. However, animals often perform poorly on it and suffer from various disorders such as "fescue foot", characterized in rough coats, weight loss, fever, tenderness or loss of hooves and tails and sometimes death; "bovine fat necrosis", characterized in hard masses of fat along the intestinal tract resulting in digestive upsets and difficult births; and "fescue toxicity", also called "summer slump" because of its common incidence in hot weather, characterized in poor weight gain, reduced conception weights and intolerance to heat.

Higher levels of incidence to fescue toxicosis have been observed in fields infected with certain fungi, in particular endophytic fungi (See Schmidt et al. *Journal of Animal Science* 55 1260-1263 (1982) Hoveland et al. *Agronomy Journal* 72 pg 375-377 (1980) and Hoveland et al. Circular 270 from Alabama Agricultural Experiment Station, Auburn University, Alabama (1984)). Certain researchers have compared pastures of tall fescue with and without contamination by the fungus *Acremoniun coenophialum* and observed a decrease in performance and weight gains and an increase in typical symptoms of fescue toxicosis in pasture with higher levels of *A coenophialum* contamination (See Hoveland et al. *Agronomy Journal* 75 pg 821-824 (1983) and Pedersen et al. *New Zealand Journal of Experimental Agriculture* 14 pg 307-312 (1986)).

The endophyte infection of tall fescue is very wide spread and the fungus is found in the fescue seeds. Thus, the fungal infection is carried over from one season to the next and has been found very difficult to eradicate. Current methods of endophyte control to prevent fescue toxicosis require fields to be chemically treated to destroy the fescue and then planted with other crop for 1,2 or more seasons to allow any residual seeds and their fungal contamination to be killed. Then the field must be planted with seeds specially grown to be free of endophyte contamination. Such procedures are obviously very labor intensive and costly and often will exceeds the savings resulting from the elimination of fescue toxicosis from pasture fed animals. Any savings that might result may then be defeated if the field is later reinfected with the fungus. Obviously the economical treatment of fescue toxicosis has long been a goal of breeders and growers of pasture fed livestock.

Ivermectin is a semi-synthetic member of the class of compounds known as avermectins which are macrocyclic esters which have been discovered to be highly potent antiparasitic agents for animals of both endo and ectoparasites. The compounds have further been found to be highly active as an agricultural pesticide and nematocides against insects which parasitize the aereal parts and roots of growing plants as well as stored agricultural products. Avermectin compounds however are not fungicidal and no reports of any fungicidal activity have been found.

SUMMARY OF THE INVENTION

This invention concerns the novel and unexpected utility of avermectin compounds, in particular ivermectin, to prevent the effects of fescue toxicosis in animals grazing on tall fescue infected with fungi. Thus, it is an object of this invention to describe such new utility and the avermectin compounds possessing it. A further object is to describe methods of administering such avermectin compounds to grazing animals. Further objects will become apparent from a reading of the following description.

DESCRIPTION OF THE INVENTION

Avermectin compounds have been discovered to significantly reduce or eliminate the toxic effects upon grazing animals, particularly ruminants, when tall fescue infected with fungi is ingested. The avermectin compounds are a series of compounds derived from the original avermectin natural products isolated from a fermentation broth and described in U.S. Pat. No. 4,310,519 to Albers-Schonberg et al. The avermectins are isolated as four pairs of compounds and the pair identified by B1a/B1b is the most preferred. The preferred 22,23-dihydro derivatives of the avermectins are disclosed in U.S. Pat. No. 4,199,569 to Chabala et al. and the 22,23-dihydro avermectin B1a/B1b pair of compounds in an approximately 80:20 mixture are most preferred and are known as ivermectin.

Other avermectin derivatives are useful in preventing fescue toxicosis such as the monosaccharide and aglycone derivatives disclosed in U.S. Pat. No. 4,206,205 to Mrozik et al; the acylated derivatives thereof such as those disclosed in U.S. Pat. No. 4,201,861 to Mrozik et al; the 13-deoxy aglycone compounds disclosed in U.S. Pat. Nos. Re. 32034 and Re. 32006 to Chabala et al; and the 4"-keto and 4"-amino compounds disclosed in U.S. Pat. No. 4,427,663 to Mrozik.

Additional compounds usable as in preventing fescue toxicosis are the milbemycin compounds disclosed in U.S. Pat. No. 3,950,360 to Aoki et al. and the oxime derivates thereof disclosed in U.S. Pat. No. 4,547,520 to Ide et al.

The preferred avermectin compounds for use in preventing fescue toxicosis are realized in the following structural formula:

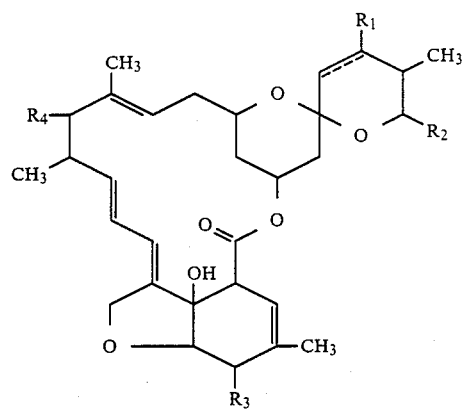

wherein the broken line indicates a single or double bond;

$R_1$ is H, =O, loweralkanoyloxy or OH, provided that $R_1$ is present only when the broken line indicates a single bond;

$R_2$ is methyl, ethyl, isopropyl or sec-butyl;

$R_3$ is OH, $OCH_3$ or loweralkanoyloxy;

$R_4$ is H, OH, loweralkanoyloxy, α-L-oleandrosyloxy, 4'-(α-L-oleandrosyl)-α-L-oleandrosyloxy, 4'-loweralkanoyl-α-L-oleandrosyloxy, 4''-loweralkanoyl-4'-(α-L-oleandrosyl)-α-L-oleandrosyloxy, 4''-amino-4'-(α-L-oleandrosyl)-α-L-oleandrosyloxy, 4''-mono- or diloweralkylamino-4'-(α-L-oleandrosyl)-α-L-oleandrosyloxy, and physiologically acceptable salts thereof.

The preferred milbemycin compounds for use as growth promotion agents are realized in the following formula:

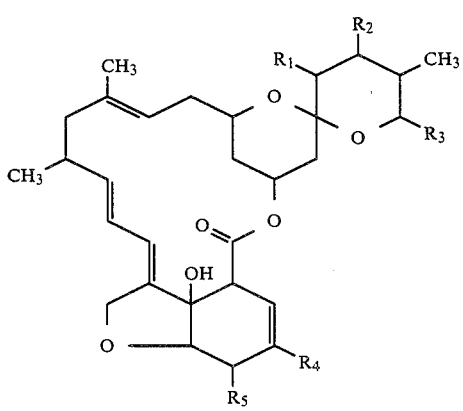

wherein the various R groups have the following meanings:

| $R_1$ | $R_2$ | $R_3$ | $R_4$ | $R_5$ |
|---|---|---|---|---|
| H | H | $CH_3$ | $CH_3$ | OH |
| H | H | $CH_3$ | $CH_3$ | $OCH_3$ |
| H | H | $C_2H_5$ | $CH_3$ | OH |
| H | H | $C_2H_5$ | $CH_3$ | $OCH_3$ |
| OH | $-O-\overset{\overset{O}{\|\|}}{C}-\overset{\overset{CH_3}{\|}}{CH}-C_4H_9$ | $CH_3$ | $CH_3$ | OH |
| OH | $-O-\overset{\overset{O}{\|\|}}{C}-\overset{\overset{CH_3}{\|}}{CH}-C_4H_9$ | $CH_3$ | $CH_3$ | $OCH_3$ |
| OH | $-O-\overset{\overset{O}{\|\|}}{C}-\overset{\overset{CH_3}{\|}}{CH}-C_4H_9$ | $C_2H_5$ | $CH_3$ | OH |
| OH | $-O-\overset{\overset{O}{\|\|}}{C}-\overset{\overset{CH_3}{\|}}{CH}-C_4H_9$ | $C_2H_5$ | $CH_3$ | $OCH_3$ |
| H | H | $CH_3$ | $-CH_2-OC(=O)-\text{pyrrole-NH}$ | OH |
| H | H | $C_2H_5$ | $-CH_2-OC(=O)-\text{pyrrole-NH}$ | OH |
| H | H | $i-C_3H_7$ | $-CH_2-OC(=O)-\text{pyrrole-N}$ | OH |
| H | H | $CH_3$ | $CH_3$ | $=N-OR_6$ |
| H | H | $C_2H_5$ | $CH_3$ | $=N-OR_6$ |
| H | H | $i-C_3H_7$ | $CH_3$ | $=N-OR_6$ | wherein $R_6$ is hydrogen or loweralkyl.

The term "loweralkyl" when used in the instant application is intended to represent those alkyl groups either straight or branched chain which have from 1-5 carbon atoms. Examples of such alkyl groups are methyl, ethyl, propyl, iso-propyl, butyl, sec-butyl, pentyl, and the like.

The term "loweralkanoyl" is intended to include those alkanoyl groups containing from one to five carbon atoms in either a straight or branched chain. Examples of such alkanoyl groups are formyl, acetyl, propionyl, butyryl, valeryl, and the like.

The "b" compounds, those with a 25-isopropyl group, are often not separated from the closely related "a" compounds with a 25-sec-butyl group since the physical and chemical properties of such compounds are similar, and as such the compounds are generally isolated as mixtures of the two compounds. Thus references in the instant application to "a" compounds such as B1a, A1a, and the like, are construed to define the pure compound as well as those which actually contain a certain proportion of the corresponding "b" compound. Alternatively, this representation of a mixture is sometimes done by referring to the compounds without designating "a" or "b" such as in the A1 or B2 compounds, or by separating the "a" compound from the "b" compound by a slash (/) such as B1a/B1b, B2a/B2b and the like.

The avermectin compounds can be used to prevent and treat the effects of fescue toxicosis in ruminant and non-ruminant animals such as sheep, cattle, goats, horses, that are pastured in fields of tall fescue. The active compound can be fed to the animal by incorporating it into the animal's feed or drinking water or it can be administered in a unit dosage form either orally as a drench, tablet, bolus or sustained release bolus or parenterally by injection or from a subcutaneous implant, or by a topically applied solution or suspension. The administration of the active compounds will allow the amimal to fully utilize the nutritional content of tall fescue, generally considered to be nutritionally adequate for maintenance and growth, without any of the manifestations of fescue toxicosis such as "fescue foot", "bovine fat necrosis" summer slump"and the like.

The active compounds can be administered to the animals at daily rates of from 0.004 to 2.0 mg/kg of body weight which may vary depending upon the particular animal being treated as well as the age and general physical condition of the animal. Preferably, daily dosages of from 0.04 to 1.0 mg/kg are utilized. When administered as part of the animal's feed or drinking water the active compound is present at rates of from 0.1 to 100 ppm which is determined to provide the appropriate daily amounts of the growth promotant compound.

The effects of an avermectin compound (ivermectin) in preventing symptoms of fescue toxicosis have been observed in field trials of cattle grazing on tall fescue highly infected (85%) with an endophytic fungus. The control animals showed classic signs of fescue toxicosis, reduced weight gain, poor coats, heat intolerance, fever and the like. The treated animals were given a sustained release bolus prior to grazing containing sufficient ivermectin for 120 days at from 0.04 to 0.06 mg/kg per day. The treated cattle gained an average of 39.6 kg more than the untreated cattle and further did not show any signs of fescue toxicosis. By visible examination, the treated cattle could be distinguished from the untreated cattle by observing their larger size, better coat and better disposition. In addition, the treated cattle had better appetites than the untreated cattle and grazed for longer periods of time, particularly in warmer weather when the effects of heat intolerance were becoming more apparent in the untreated cattle.

The test demonstrates the significant effects ivermectin and other avermectin and milbemycin compounds have on the elimination of the symptoms of fescue toxicosis.

In a further test, cattle were grazed on paddocks of tall fescue with high levels of endophyte fungal infection. After 120 days the cattle continuosly treated with ivermectin from a sustained release bolus gained an average of 28 kg more than the untreated cattle; about one-quarter of a kilogram per day over the controls. In this test the control cattle had a very low level parasite burden, thus any weight gains not observed would have to be due to fescue toxicosis, thus demonstrating the efficacy of the instant compounds in preventing toxic effects of such infected grasses.

What is claimed is:

1. A method for treating the symptoms of fescue toxicosis in animals ingesting tall fescue infected with an endophytic fungus which comprises administering to such animals an effective amount of an avermectin or a milbemycin compound.

2. The method of claim 1 wherein the active compound has the formula:

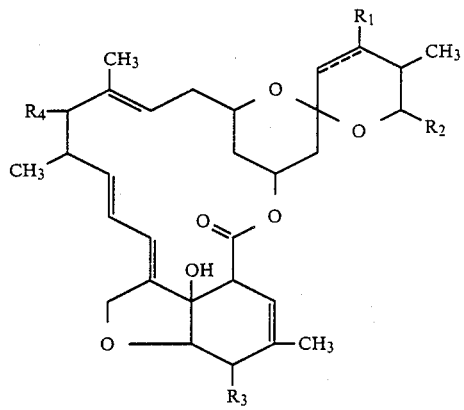

wherein the broken line indicates a single or double bond;

$R_1$ is H, =O, loweralkanoyloxy or OH, provided that $R_1$ is present only when the broken line indicates a single bond;

$R_2$ is methyl, ethyl, isopropyl or sec-butyl;

$R_3$ is OH, $OCH_3$ or loweralkanoyloxy;

$R_4$ is H, OH, loweralkanoyloxy, α-L-oleandrosyloxy, 4'-(α-L-oleandrosyl)-α-L-oleandrosyloxy, 4'-loweralkanoyl-α-L-oleandrosyloxy, 4''-loweralkanoyl-4'-(α-L-oleandrosyl)-α-L-oleandrosyloxy, 4''-amino-4'-(α-L-oleandrosyl)-α-L-oleandrosyloxy, 4''-mono- or diloweralkylamino-4'-(α-L-oleandrosyl)-α-L-oleandrosyloxy, and physiologically acceptable salts thereof.

3. The method of claim 2 wherein the active compound is ivermectin.

4. The method of claim 1 wherein the active compound has the formula:

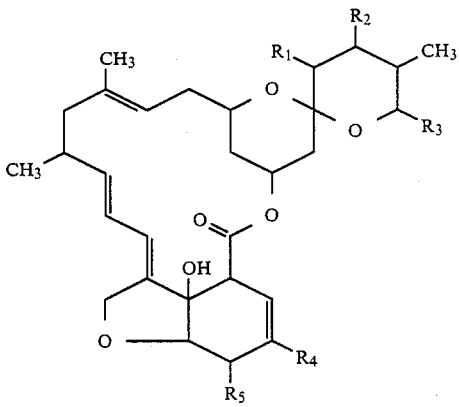

wherein the compounds are determined when $R_1$, $R_2$, $R_3$, $R_4$ and $R_5$ have the following meanings:

| $R_1$ | $R_2$ | $R_3$ | $R_4$ | $R_5$ |
|---|---|---|---|---|
| H | H | $CH_3$ | $CH_3$ | OH |
| H | H | $CH_3$ | $CH_3$ | $OCH_3$ |
| H | H | $C_2H_5$ | $CH_3$ | OH |
| H | H | $C_2H_5$ | $CH_3$ | $OCH_3$ |
| OH | $-O-C(=O)-CH(CH_3)-C_4H_9$ | $CH_3$ | $CH_3$ | OH |
| OH | $-O-C(=O)-CH(CH_3)-C_4H_9$ | $CH_3$ | $CH_3$ | $OCH_3$ |
| OH | $-O-C(=O)-CH(CH_3)-C_4H_9$ | $C_2H_5$ | $CH_3$ | OH |
| OH | $-O-C(=O)-CH(CH_3)-C_4H_9$ | $C_2H_5$ | $CH_3$ | $OCH_3$ |
| H | H | $CH_3$ | $-CH_2-OC(=O)-(\text{pyrrole-NH})$ | OH |
| H | H | $C_2H_5$ | $-CH_2-OC(=O)-(\text{pyrrole-NH})$ | OH |
| H | H | $i$-$C_3H_7$ | $-CH_2-OC(=O)-(\text{pyrrole-N})$ | OH |
| H | H | $CH_3$ | $CH_3$ | $=N-OR_6$ |
| H | H | $C_2H_5$ | $CH_3$ | $=N-OR_6$ |
| H | H | $i$-$C_3H_7$ | $CH_3$ | $=N-OR_6$ | wherein $R_6$ is hydrogen or loweralkyl.

5. The method of claim 1 wherein the active compound is administered at a dosage of from 0.02 to 2.0 mg/kg/day of the animal's body weight.

6. The method of claim 5 wherein the active compound is administered at a dosage of from 0.1 to 1.0 mg/kg/day of the animal's body weight.

7. The method of claim 1 wherein the active compound is topically or orally administered.

8. The method of claim 7 wherein the active compound is administered in the animal's feed or drinking water.

9. The method of claim 7 wherein the active compound is orally administered in a unit dosage form selected from a drench, tablet, bolus or sustained release bolus.

10. The method of claim 1 wherein the active compound is parenterally administered.

11. The method of claim 10 wherein the active compound is administered as a subcutaneous implant.